US00PP33753P2

(12) United States Plant Patent
Meilland

(10) Patent No.: US PP33,753 P2
(45) Date of Patent: Dec. 21, 2021

(54) HYBRID TEA ROSE PLANT NAMED 'MEIFFABLE'

(50) Latin Name: *Rosa hybrida*
Varietal Denomination: MEIFFABLE

(71) Applicant: THE CONARD PYLE COMPANY, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/322,253

(22) Filed: May 17, 2021

(30) Foreign Application Priority Data

May 6, 2021 (QZ) ..... PBR 2021/1234

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./101, 130, 137
See application file for complete search history.

(56) References Cited

U.S. PATENT DOCUMENTS

PP11,660 P 11/2000 Meilland
PP22,764 P3 6/2012 Meilland

*Primary Examiner* — Susan McCormick Ewoldt
*Assistant Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of hybrid tea rose plant, referred to by its cultivar name, 'MEIFFABLE', is disclosed. The new variety forms attractive, flat cup shaped, pink colored flowers. Attractive, dense, dark, and glossy foliage is formed, which contrasts beautifully with the blossoms. An erected growth habit is displayed. The new variety is well suited for providing attractive ornamentation in the landscape.

1 Drawing Sheet

Botanical/commercial classification: Latin name—*Rosa hybrida.*

Varietal denomination: 'MEIFFABLE'.

CROSS-REFERENCE TO RELATED APPLICATIONS

This application claims priority to Plant Breeders' Right Application Number 2021/1234, which was filed at Community Plant Variety Office in the European Union on May 6, 2021, the contents of which are hereby incorporated by reference for all purposes.

SUMMARY OF THE INVENTION

The new variety of *Rosa hybrida* plant was created by artificial pollination wherein two parents were crossed which previously had been studied in the hope that they would contribute the desired characteristics. The female parent (i.e., the seed parent) was the 'MEIKOLYMA' variety (U.S. Plant Pat. No. 22,764). The male parent (i.e., the pollen parent) was an unnamed seedling (non-patented) which was the product from the cross between another unnamed seedling (non-patented) and the 'MEIZINCARO' variety (U.S. Plant Pat. No. 11,660).

The parentage of the new variety can be summarized as follows:

'MEIKOLYMA' x (Unnamed Seedling x 'MEIZINCARO')

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) emits a strong fruity fragrance,
(b) forms pink colored blossoms, and
(c) exhibits a dark green, glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEIKOLYMA' variety (i.e., the seed parent) produces flowers which are less fragrant compared to the new variety. The male unnamed seedling variety parent (i.e., the pollen parent) displays ochre and margined with pink colored flowers, whereas the new variety displays pink colored flowers. Moreover, the new variety can be readily distinguished from other similar non-parental varieties. For example, the 'MEIKERIRA' variety (not patented) displays a less compact growth habit compared to the growth habit of new variety.

The new variety has been found to undergo asexual propagation in Le Cannet des Maures, Var, France by a number of routes, including eye budding, softwood cuttings, hardwood cuttings, and semi-hardwood cuttings. Asexual propagation by the above-mentioned techniques in Le Cannet des Maures, Var, France has shown that the characteristics of the new variety are stable and are strictly transmissible by such asexual propagation from one generation to another. Accordingly, the new variety undergoes asexual propagation in a true-to-type manner.

The new variety has been named 'MEIFFABLE'.

The first offer for sale of the new variety was May 27, 2020 in The Netherlands by the inventor or another who obtained the new variety directly or indirectly from the inventor.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during May while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—observe.

Element 8—illustrates a specimen of a fully open flower—plan view—reverse.

Element 9—illustrates a specimen of a fully open flower—plan view—observe.

Element 10—illustrates a specimen of a flowering stem.

Element 11—illustrates a specimen of a floral receptacle showing arrangement of the stamens and pistils.

Element 12—illustrates a specimen of a floral receptacle showing arrangement of the pistils (stamens removed).

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of one-year-old specimens of the new variety during May while budded on their own roots and growing outdoors at Le Cannet des Maures, Var, France.

Commercial classification: Hybrid Tea Rose Plant.

Plant:

*Habit.*—Erected.

*Height.*—Between 50 to 100 cm on average.

*Width.*—Between 30 to 40 cm on average.

Branches:

*Color.*—Young stems: commonly near Green Group 143A amply covered on some places with near Greyed-Purple Group 184A. — adult wood: commonly near Yellow-Green Group 146A slightly mixed with near Green Group 143A.

*Length.*—From the crown to the flower: between 60 cm to 80 cm on average.

*Diameter.*—Approximately 0.5 cm on average.

*Internode.*—Number on the entire branch: between 10 to 15 on average. — length: between 3.0 cm to 9.0 cm on average.

*Thorns.*—Configuration on adult stems: concave and elongated on the upper surface and concave on the under surface. — long prickles — quantity: commonly between 10 to 15 thorns per 15 cm long young stem and commonly between 20 to 30 thorns per 15 cm long adult stem. — long prickles — base shape: broad obovate on young stems and narrow obovate on adult stems. — long prickles — size: between 0.8 cm to 1.1 cm in length on average on young stems and between 0.5 cm to 1.0 cm in length on average on adult stems. — long prickles — color: commonly near Yellow-Green Group 144B covered with near Greyed-Purple Group 185B except for the tip of the thorns on young stems; and commonly near Yellow-Green Group 144B more or less suffused with near Greyed-Purple Group 185B on adult stems. — small prickles, under 0.7 cm in length — quantity: absent.

Foliage:

*General Appearance.*—Dense with glossy aspect.

*Number of leaflets.*—3, 5, and 7; most often 5.

*5 leaflets leaf.*—Length: approximately 21 cm on average. — width: approximately 16 cm on average.

*New foliage.*—Upper surface color: commonly a mix between near Green Group 141A and Yellow-Green Group 144A. — under surface color: commonly near Yellow-Green Group 148B with some reflects near Greyed-Purple Group 185B.

*Adult foliage.*—Upper surface color: commonly near Green Group 139A. — under surface color: commonly near Green Group 138A.

Leaflets:

*Shape.*—Tip: acuminate. — base: rounded.

*Glossiness of upper surface.*—Intensity is strong.

*Terminal leaflet.*—Length: approximately 9.5 cm on average. — width: approximately 6.0 cm on average.

*Texture.*—Leathery.

*General appearance.*—Elliptical.

*Serration.*—Small and single.

*Undulation on the margin.*—Weak.

*Petiole rachis.*—Color of upper surface: commonly near Green Group 143B bordered with Green Group 139A. — color of under surface: commonly near Green Group 143B. — texture: smooth. — rachis length of terminal leaflet: approximately 5.5 cm on average. — rachis diameter of terminal leaflet: approximately 0.3 cm on average.

*Petioles.*—Upper surface: not glandular. — under surface: few prickles. — general appearance: adnate, pectinate and narrow. — color of upper surface: commonly near Green Group 143B slightly bordered with Green Group 139A. — color of under surface: commonly near Green Group 143B. — petiole length: approximately 5.5 cm on average. — petiole diameter: approximately 0.3 cm on average.

*Stipules.*—Length: approximately 2.0 cm on average. — width: approximately 0.4 cm on average. — color of upper surface: commonly near Green Group 143B with sometimes on the center near Greyed-Red Group 181C. — color of under surface: commonly near Green Group 143B slightly blended with near Green Group 141B.

Inflorescence:

*Number of flowers per stem.*—Typically 1 flower per stem.

*Lastingness of the bloom.*—On the plant: approximately 7 days on average. — in vase: approximately 10 days.

*Bud.*—Shape: globular. — size: medium. — length: between 4.0 cm to 5.0 cm on average. — width: between 4.0 cm to 5.0 cm on average. — color as calyx breaks: upper surface: commonly near Red-Purple Group 65C bordered and suffused with near Red-Purple Group 68C and suffused with a blend on Orange-Red Group 33C and 33D approaching the basal spot; basal spot commonly near Yellow Group 7A. under surface: commonly mix of near Red-Purple Group 68C and Red Group 43D.

*Sepals.*—Number: commonly 5. — length: approximately 3.0 cm on average. — width: approximately 1.4 cm on average. — shape: at the top: elongated and narrow, extensions: commonly 3 sepals have medium extensions and the other two do not. — upper surface: texture: tomentous. color commonly near Yellow-Green Group 145D bordered with near Green Group 138C. — under surface: texture: tomentous. color: commonly near Green Group 143C.

*Receptacle.*—Color: commonly near Green Group 143B. — length: approximately 1.0 cm on average. — width: approximately 1.5 cm to 2.0 cm on average. — surface: smooth. — shape: broad funnel shaped.

*Peduncle.*—Length: between 8 cm to 13 cm on average. — width: approximately 0.6 cm on average. — surface: glandular. — color commonly a blend between near Green Group 143A and Green Group 143B.

*Flower.*—Average size when fully open: between 10 cm to 15 cm on average. — shape: flat cup shaped. — shape when viewed from above: rounded. — type: very double. — number of petals under normal conditions: typically between 100 to 150 petals. — shape of the petal: base: acute and broad. top: cordiform. — undulation of the petal: weak. — reflexing of the petal: very weak. — petal incision: medium. — texture of the petal: thick. — petal length: between 2.0 cm to 5.0 cm on average. — petal width: between 1.5 cm to 5.0 cm on average. — arrangement: imbricated with some petaloids (same shape as the petals, but curled up). — petal drop: petals drop off cleanly before drying. — fragrance: fruity and strong. — color when opening: basal spot on upper surface: commonly near Yellow Group 7A. upper surface of the flower: external petals are commonly near Red-Purple Group 65C veined with near Yellow Group 7B on the base of the petals; and internal petals are commonly near Red-Purple Group 65C bordered and suffused with near Red-Purple Group 68C and suffused with a blend of Orange-Red Group 33C and 33D approaching the basal spot. basal spot on under surface: commonly near Yellow Group 7C. under surface of the flower: external petals are commonly near Red-Purple Group 65D ranging from Red-Purple Group 68C on the edge of the petal, with a slightly nuance of near Red Group 43D at the base; and internal petals are commonly mix from Red-Purple Group 68C and Red Group 43D. — color of the open flower: basal spot on upper surface: commonly near Yellow Group 7A. upper surface of the flower: commonly near Red-Purple Group 65C veined with near Yellow Group 7B on the base of the petals. basal spot on under surface: commonly near Yellow Group 7C. under surface of the flower: commonly near Red-Purple Group 65D ranging from Red-Purple Group 68C on the edge of the petal, with a slightly nuanced of near Red Group 43D at the base. — anthers: number is between 90 to 100 on average, length is approximately 0.3 cm on average, coloration is commonly near Yellow-Orange Group 17B, and arrangement is regular around styles. — filaments: length is approximately 0.4 cm on average and coloration is commonly near Yellow-Orange Group 17B. — styles: length is approximately 0.6 cm on average, coloration is commonly near Yellow Group 13D, and number is between 170 to 200 on average. — stigmas: size is approximately 0.1 cm on average and coloration is commonly near Yellow Group 13C. — pollen: color is commonly near Yellow-Orange Group 17A and amount is medium. — hips: not available at this stage.

Development:

*Vegetation.*—Strong.

*Blooming.*—Early in the season and intermittent, typically from May to October in France.

*USDA hardiness zone.*—Zone 5.

*Tolerance to disease.*—Good, and particularly against rust (*Phragmidium* sp.) and powdery mildew (*Podosphaera pannosa*)

The new 'MEIFFABLE' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIFFABLE' characterized by the following combination of characteristics:

(a) emits a strong fruity fragrance, (b) forms pink colored blossoms, and (c) exhibits a dark green, glossy foliage;

substantially as herein shown and described.

* * * * *

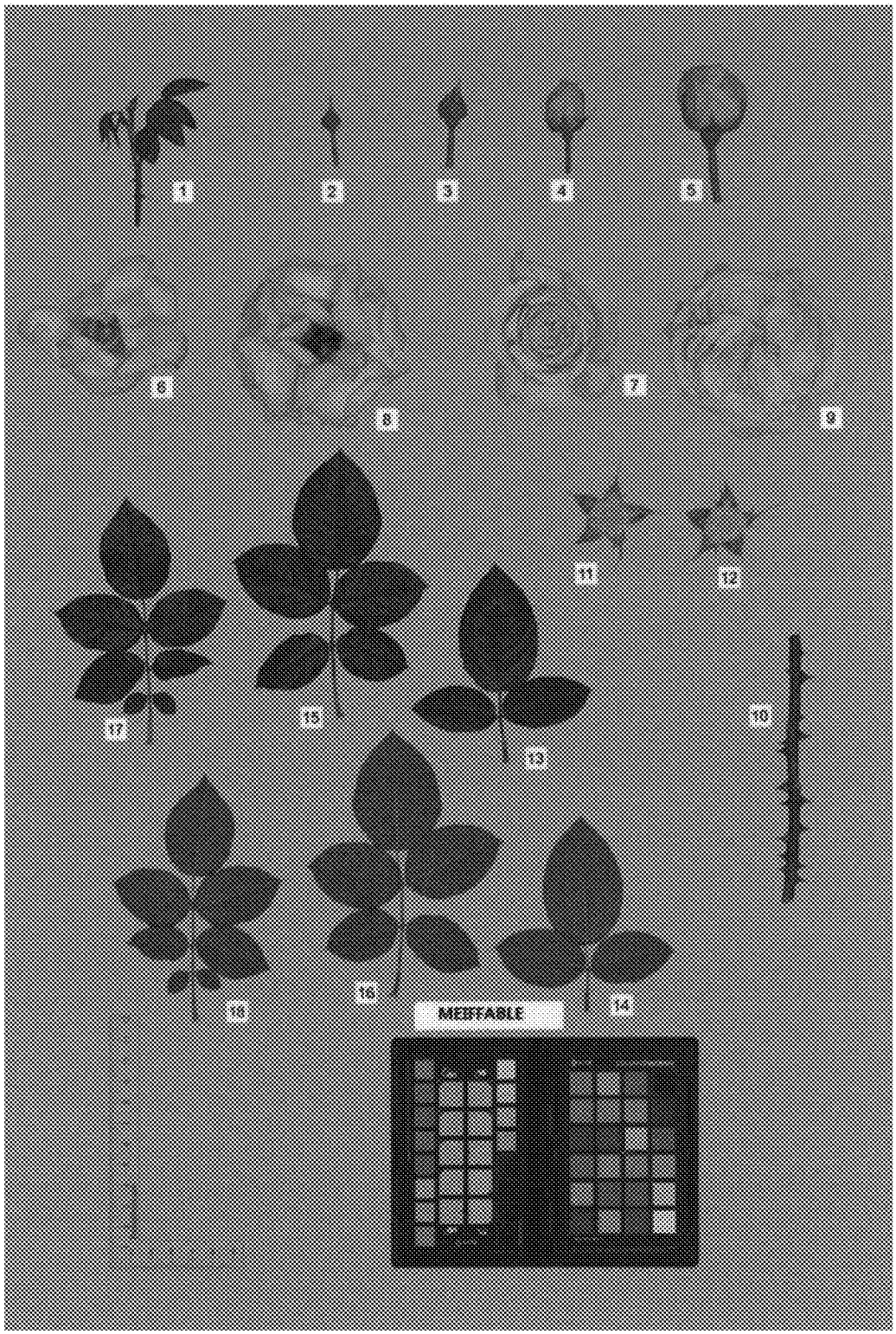
1
2
3
4
5
6
7
8
9
10
11
12
13
14
15
16
17
MEBTABLE